US009095260B2

(12) United States Patent
Nakao et al.

(10) Patent No.: US 9,095,260 B2
(45) Date of Patent: Aug. 4, 2015

(54) MEASUREMENT APPARATUS, MEASUREMENT METHOD, PROGRAM AND INFORMATION PROCESSING APPARATUS

(75) Inventors: Isamu Nakao, Tokyo (JP); Hirotaka Muramatsu, Tokyo (JP); Takayuki Ogiso, Tokyo (JP); Akira Endo, Saitama (JP)

(73) Assignee: SONY CORPORATION, Tokyo (JP)

( * ) Notice: Subject to any disclaimer, the term of this patent is extended or adjusted under 35 U.S.C. 154(b) by 527 days.

(21) Appl. No.: 13/465,386

(22) Filed: May 7, 2012

(65) Prior Publication Data

US 2012/0310071 A1 Dec. 6, 2012

(30) Foreign Application Priority Data

Jun. 3, 2011 (JP) ................................. 2011-124908

(51) Int. Cl.
*A61B 5/044* (2006.01)
*A61B 5/0408* (2006.01)
*A61B 5/00* (2006.01)
*A61B 5/053* (2006.01)

(52) U.S. Cl.
CPC ............. *A61B 5/0408* (2013.01); *A61B 5/0537* (2013.01); *A61B 5/4872* (2013.01); *A61B 5/6898* (2013.01); *A61B 5/044* (2013.01); *A61B 2560/0468* (2013.01); *A61B 2562/046* (2013.01); *A61B 2562/125* (2013.01)

(58) Field of Classification Search
CPC .................................................... A61B 5/0408
USPC .......................................... 382/115; 600/393
See application file for complete search history.

(56) References Cited

U.S. PATENT DOCUMENTS

| 6,888,536 | B2 * | 5/2005 | Westerman et al. | 345/173 |
|---|---|---|---|---|
| 7,171,680 | B2 | 1/2007 | Lange | |
| 7,689,833 | B2 | 3/2010 | Lange | |
| 8,542,208 | B2 * | 9/2013 | Krah et al. | 345/173 |
| 8,552,989 | B2 * | 10/2013 | Hotelling et al. | 345/173 |
| 8,654,083 | B2 * | 2/2014 | Hotelling et al. | 345/173 |
| 2006/0136744 | A1 | 6/2006 | Lange | |
| 2006/0227097 | A1 * | 10/2006 | Zhou et al. | 345/107 |
| 2011/0150291 | A1 * | 6/2011 | Jung | 382/115 |
| 2011/0222745 | A1 * | 9/2011 | Osterhout et al. | 382/118 |

FOREIGN PATENT DOCUMENTS

JP 2008-518709 A 6/2008

* cited by examiner

*Primary Examiner* — Samir Ahmed
(74) *Attorney, Agent, or Firm* — Hazuki International, LLC

(57) ABSTRACT

A measurement apparatus according to the present disclosure including a plurality of transparent electrodes provided on a surface of a display, an acquisition part acquiring an imaging signal obtained by imaging the surface of the display from an inside of the display, a configuring part configuring electrode pair candidates from the plurality of transparent electrodes based on the imaging signal acquired in a state that a subject touches the surface of the display, an electrocardiographic waveform signal measurement part measuring electrocardiographic waveform signals of the subject using respective electrode pair candidates configured, and a determination part determining a measurement electrode pair from the electrode pair candidates based on the electrocardiographic waveform signals measured using respective electrode pair candidates. This measurement apparatus is applicable to, for example, performing a personal authentication process of the subject based on the electrocardiographic waveform signal.

10 Claims, 10 Drawing Sheets

MEASUREMENT APPARATUS, MEASUREMENT METHOD, PROGRAM AND INFORMATION PROCESSING APPARATUS

CROSS-REFERENCE TO RELATED APPLICATION

The present application claims priority from Japanese Patent Application No. JP 2011-124908 filed in the Japanese Patent Office on Jun. 3, 2011, the entire content of which is incorporated herein by reference.

BACKGROUND

The present disclosure relates to a measurement apparatus, a measurement method, a program and an information processing apparatus, and specifically relates to a measurement apparatus, a measurement method, a program and an information processing apparatus configured to measure an electrocardiogram signal of a subject using transparent electrodes provided on a surface of a display.

Usually, an electrocardiogram (hereinafter, referred to as an electrocardiographic waveform signal) is measured in medical applications such as a medical checkup. It is known that the electrocardiographic waveform signal represents periodical movement of a heart and a waveform pattern for its one cycle (hereinafter, referred to as a heartbeat pattern) indicates a feature different from another for individuals.

And it is proposed to utilize this heartbeat pattern for personal authentication (for example, refer to National Publication of International Patent Publication No. 2008-518709).

SUMMARY

Incidentally, when performing the personal authentication utilizing the electrocardiographic waveform signal, the situation that the performing of the personal authentication is concealed from an authenticated person (a subject) is to be considered. In this case, it is desirable to provide a mechanism allowing the authenticated person to touch electrodes without causing the authenticated person to be conscious of the electrodes for measuring the electrocardiographic waveform signal.

The present disclosure is devised in view of the aforementioned circumstances and it is desirable to measure the electrocardiographic waveform signal without causing the subject to be conscious.

According to a first aspect of the present disclosure, there is provided a measurement apparatus including: a plurality of transparent electrodes provided on a surface of a display; an acquisition part acquiring an imaging signal obtained by imaging the surface of the display from an inside of the display; a configuring part configuring electrode pair candidates from the plurality of transparent electrodes based on the imaging signal acquired in a state that a subject touches the surface of the display; an electrocardiographic waveform signal measurement part measuring electrocardiographic waveform signals of the subject using respective electrode pair candidates configured; and a determination part determining a measurement electrode pair from the electrode pair candidates based on the electrocardiographic waveform signals measured using respective electrode pair candidates.

The electrocardiographic waveform signal measurement part can further measure an electrocardiographic waveform signal using the determined measurement electrode pair.

According to the first aspect of the present disclosure, there is provided the measurement apparatus which may further include an authentication processing part performing authentication process of the subject based on the measured electrocardiographic waveform signals.

The determination part may determine the measurement electrode pair from the electrode pair candidates based on S/N ratios of the measured electrocardiographic waveform signals using respective electrode pair candidates.

The determination part may determine the measurement electrode pair from the electrode pair candidates based on communication results in communications of a predetermined pattern signal via respective electrode pair candidates.

According to the first aspect of the present disclosure, there is provided the measurement apparatus which may further include a bioelectrical impedance measurement part measuring a bioelectrical impedance of the subject using the determined measurement electrode pair.

The bioelectrical impedance measurement part may further measure bioelectrical impedances of the subject using respective electrode pair candidates selected, and the determination part can further determine the measurement electrode pair from the electrode pair candidates based on the bioelectrical impedances measured using respective electrode pair candidates.

According to the first aspect of the present disclosure, there is provided a measurement method for a measurement apparatus measuring an electrocardiographic waveform signal of a subject, including, by the measurement apparatus: acquiring an imaging signal obtained by imaging a surface of a display from an inside of the display, a plurality of transparent electrodes being provided on the surface; configuring electrode pair candidates from the plurality of transparent electrodes based on the imaging signal acquired in a state that the subject touches the surface of the display; measuring electrocardiographic waveform signals of the subject using respective electrode pair candidates configured; and determining a measurement electrode pair from the electrode pair candidates based on the electrocardiographic waveform signals measured using respective electrode pair candidates.

According to the first aspect of the present disclosure, there is provided a program causing a computer to function as: an acquisition part acquiring an imaging signal obtained by imaging a surface of a display from an inside of the display, a plurality of transparent electrodes being provided on the surface; a configuring part configuring electrode pair candidates from the plurality of transparent electrodes based on the imaging signal acquired in a state that a subject touches the surface of the display; an electrocardiographic waveform signal measurement part measuring electrocardiographic waveform signals of the subject using respective electrode pair candidates configured; and a determination part determining a measurement electrode pair from the electrode pair candidates based on the electrocardiographic waveform signals measured using respective electrode pair candidates.

In the first aspect of the present disclosure, an imaging signal obtained by imaging a surface of a display from an inside of the display, a plurality of transparent electrodes being provided on the surface, is acquired; electrode pair candidates from the plurality of transparent electrodes based on the imaging signal acquired in a state that a subject touches the surface of the display are configured; electrocardiographic waveform signals of the subject using respective electrode pair candidates configured are measured; and a measurement electrode pair from the electrode pair candidates based on the electrocardiographic waveform signals measured using respective electrode pair candidates is determined.

According to a second aspect of the present disclosure, there is provided an information processing apparatus including: a plurality of transparent electrodes provided on a surface of a display; an acquisition part acquiring an imaging signal obtained by imaging the surface of the display from an inside of the display; a configuring part configuring electrode pair candidates from the plurality of transparent electrodes based on the imaging signal acquired in a state that a subject touches the surface of the display; an electrocardiographic waveform signal measurement part measuring electrocardiographic waveform signals of the subject using respective electrode pair candidates configured or a measurement electrode pair to be determined; a determination part determining the measurement electrode pair from the electrode pair candidates based on the electrocardiographic waveform signals measured using respective electrode pair candidates; and a signal processing part performing a predetermined process based on the electrocardiographic waveform signal measured using the measurement electrode pair.

In the second aspect of the present disclosure, an imaging signal obtained by imaging a surface of a display from an inside of the display is acquired; electrode pair candidates from a plurality of transparent electrodes based on the imaging signal acquired in a state that a subject touches the surface of the display are configured; a measurement electrode pair from the electrode pair candidates based on the electrocardiographic waveform signals measured using respective electrode pair candidates is determined; and a predetermined process based on an electrocardiographic waveform signal measured using the measurement electrode pair is performed.

According to the first aspect of the present disclosure, the electrocardiographic waveform signal may be measured without causing the subject to be conscious.

According to the second aspect of the present disclosure, predetermined processes based on the electrocardiographic waveform signal of the subject may be performed.

DETAILED DESCRIPTION OF THE EMBODIMENT(S)

Hereinafter, preferred embodiments for implementing the present disclosure will be described in detail with reference to the accompanying drawings.

1. Embodiments

Summary of the Present Disclosure

Figure 1:
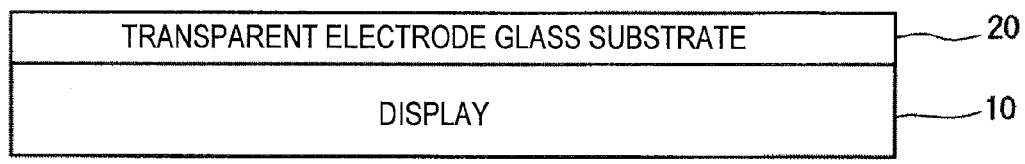
FIG. 1 is a lateral view of a display on which transparent electrodes are provided.

First, a display which serves as a display device of a measurement apparatus according to an embodiment and also has a function as an input device is described. FIG. 1 illustrates a lateral face of the display. As illustrated in the figure, in the display 10, a transparent electrode glass substrate 20 is provided on its surface. The transparent electrode glass substrate 20 is adapted to transmit visible light and near-infrared light and hardly to be recognized by a subject viewing.

Figure 2:
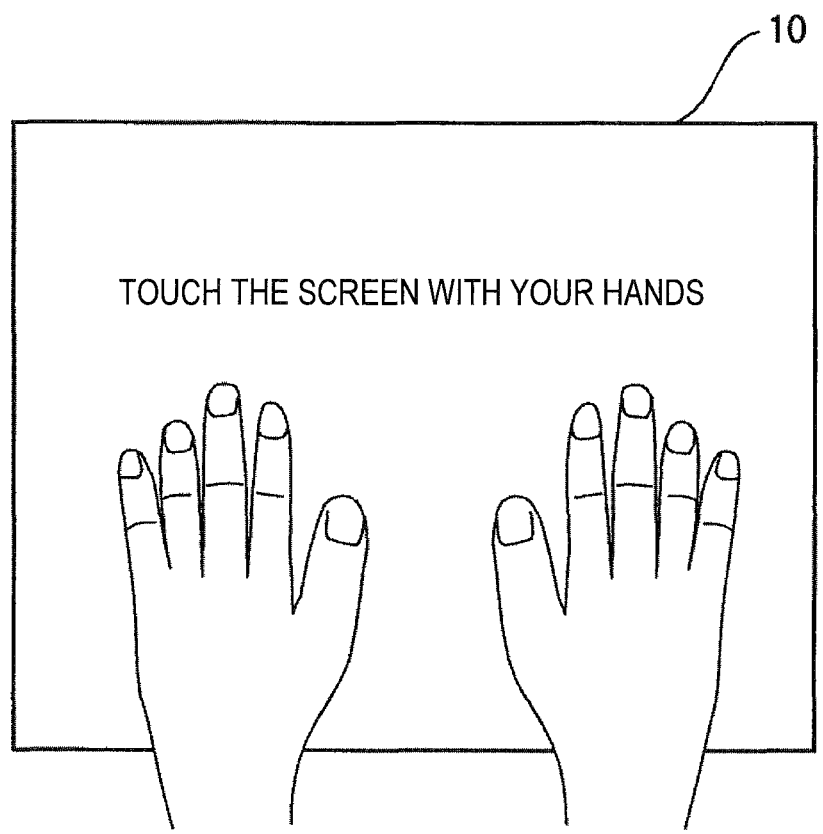
FIG. 2 is a diagram illustrating one example of screen display by a measurement apparatus.

FIG. 2 illustrates one example of screen display by a measurement apparatus. Displaying "Touch the Screen with Your Hands" on the screen of the display 10 as a guidance for the subject, for example as illustrated in the figure, can allow the subject to touch the transparent electrode glass substrate 20 with right and left palms without causing the consciousness of its presence. In addition, arms, elbows or the like instead of the palms can be used for measuring an electrocardiographic waveform signal. Moreover, voice may be used for the guidance for the subject.

The measurement apparatus according to the embodiment measures the electrocardiographic waveform signal of the subject touching the transparent electrode glass substrate 20, and using the measured electrocardiographic waveform signal, performs personal authentication of the subject. Further, the measurement apparatus also measures a bioelectrical impedance of the subject, and based on the measurement result, can present a body composition of the subject.

(Constitutional Example of the Transparent Electrode Glass Substrate)

Figure 3:
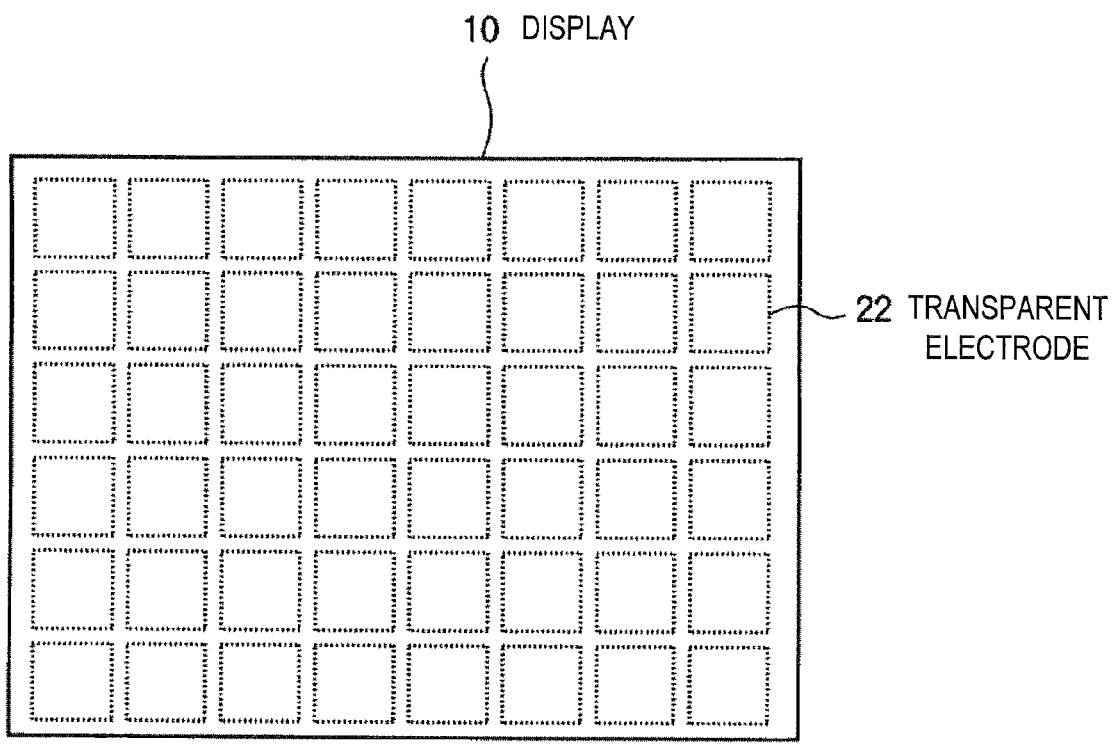
FIG. 3 is a top view illustrating transparent electrodes of a transparent electrode glass substrate.
Figure 4:
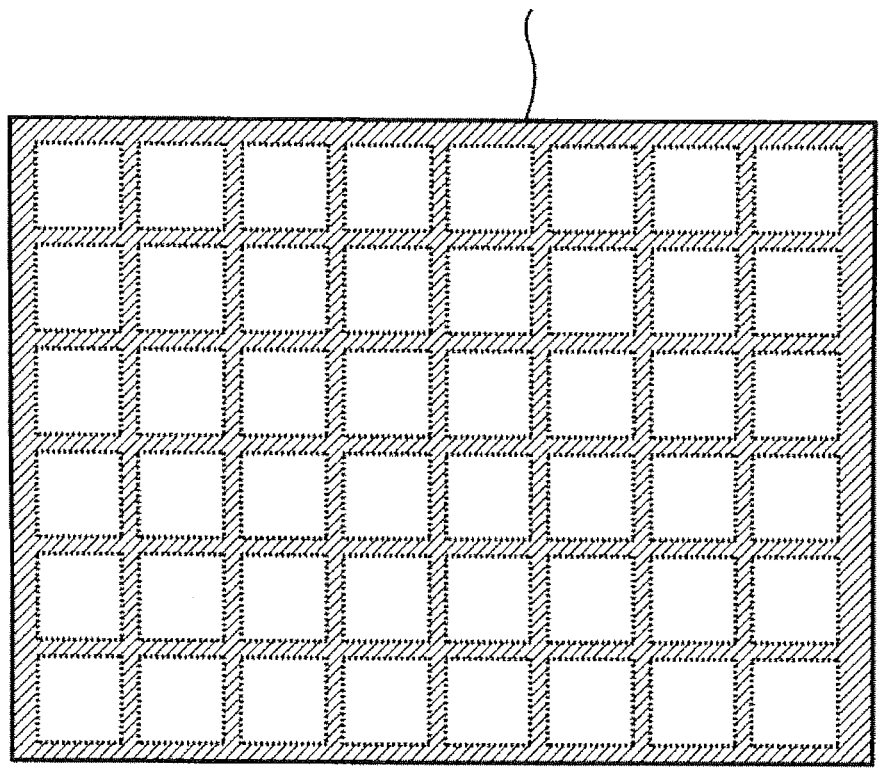
FIG. 4 is a top view illustrating an insulation film of the transparent electrode glass substrate.

FIG. 3 and FIG. 4 illustrate a top view of the transparent electrode glass substrate 20. As illustrated in FIG. 3, in the transparent electrode glass substrate 20, square transparent electrodes 22 with sides of 20 mm are arranged at an interval of 100 μm. In addition, a shape, size and interval of the transparent electrodes 22 are not limited to this. The transparent electrodes 22 are connected to a switch 52 (FIG. 7) of a measurement apparatus 50 described below. Between respective transparent electrodes 22, as illustrated in FIG. 4, an insulation film 24 is provided.

Figure 5:
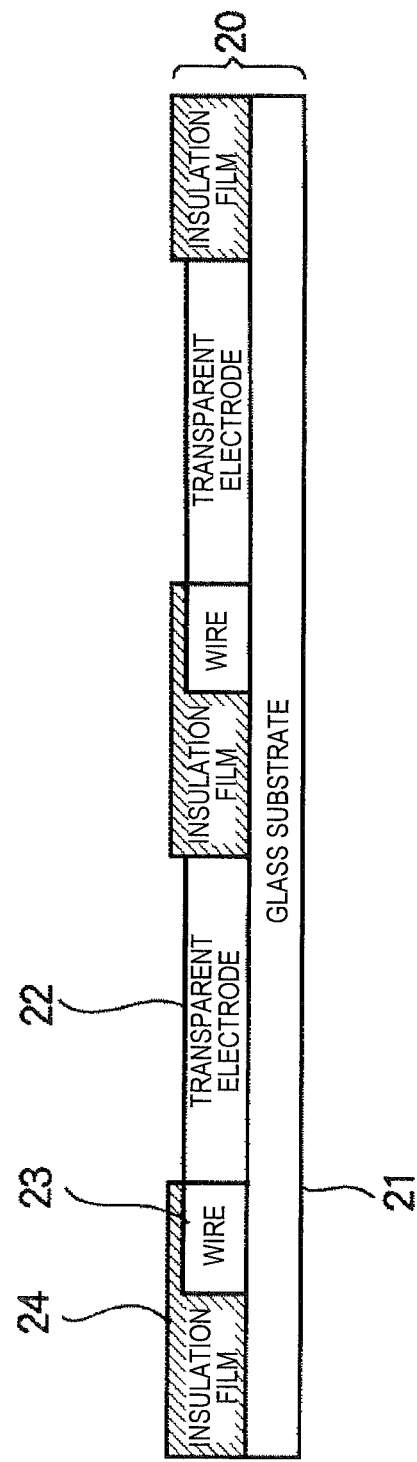
FIG. 5 is a cross-sectional view of the transparent electrode glass substrate.

FIG. 5 illustrates a cross-sectional view of the transparent electrode glass substrate 20. As illustrated in the figure, in the transparent electrode glass substrate 20, the transparent electrodes 22 and wires 23 of ITO and the insulation film 24 of $SiO_2$ are deposited on the glass substrate 21 by patterning.

Although the transparent electrodes 22 and wires 23 cause multiple interference due to an ITO film thickness, when the ITO film thickness of the transparent electrodes 22 and wires 23 is, for example, 150 nm and an $SiO_2$ film thickness of the insulation film 24 is, for example, 180 nm, thereby, reflectivities of the transparent electrode 22 and wires 23 and the insulation film 24 in a visible light zone are minimum (4%) and transmittances of those are maximum (96%). Thus, each of the reflectivities and transmittances of both can be made substantially equal. Therefore, the transparent electrodes 22 and wires 23 and the insulation film 24 can be made hardly visible from the subject.

In addition, for the transparent electrodes 22 and wires 23, semiconductor with a bandgap larger than the visible light region such as ZnO, $Ga_2O_3$, GaN and AlN, material which is made by adding impurity to those, a metal thin film which is sufficiently thin for transmitting light, a thin film of transition metal such as Mg, Al, Ti, Fe, Cr, Ni, Cu and Zn, noble metal such as Au, Ag, Pt and Pd, lanthanides other than radioisotope elements, and alloy or intermetallic compounds of these, a thin film of material with conductivity by n-conjugation electrons such as graphene and carbon nanotubes, macromolecular organic conductive material, low-molecular organic conductive material, or the like may be used instead of ITO.

When using graphene for the transparent electrodes and wires 23, the multiple interference does not arise. Accordingly, the $SiO_2$ film thickness of the insulation film 24 is arbitrary and can be made thin down to its lower limit at which the insulation is maintained.

(Constitutional Example of the Display)

Figure 6:
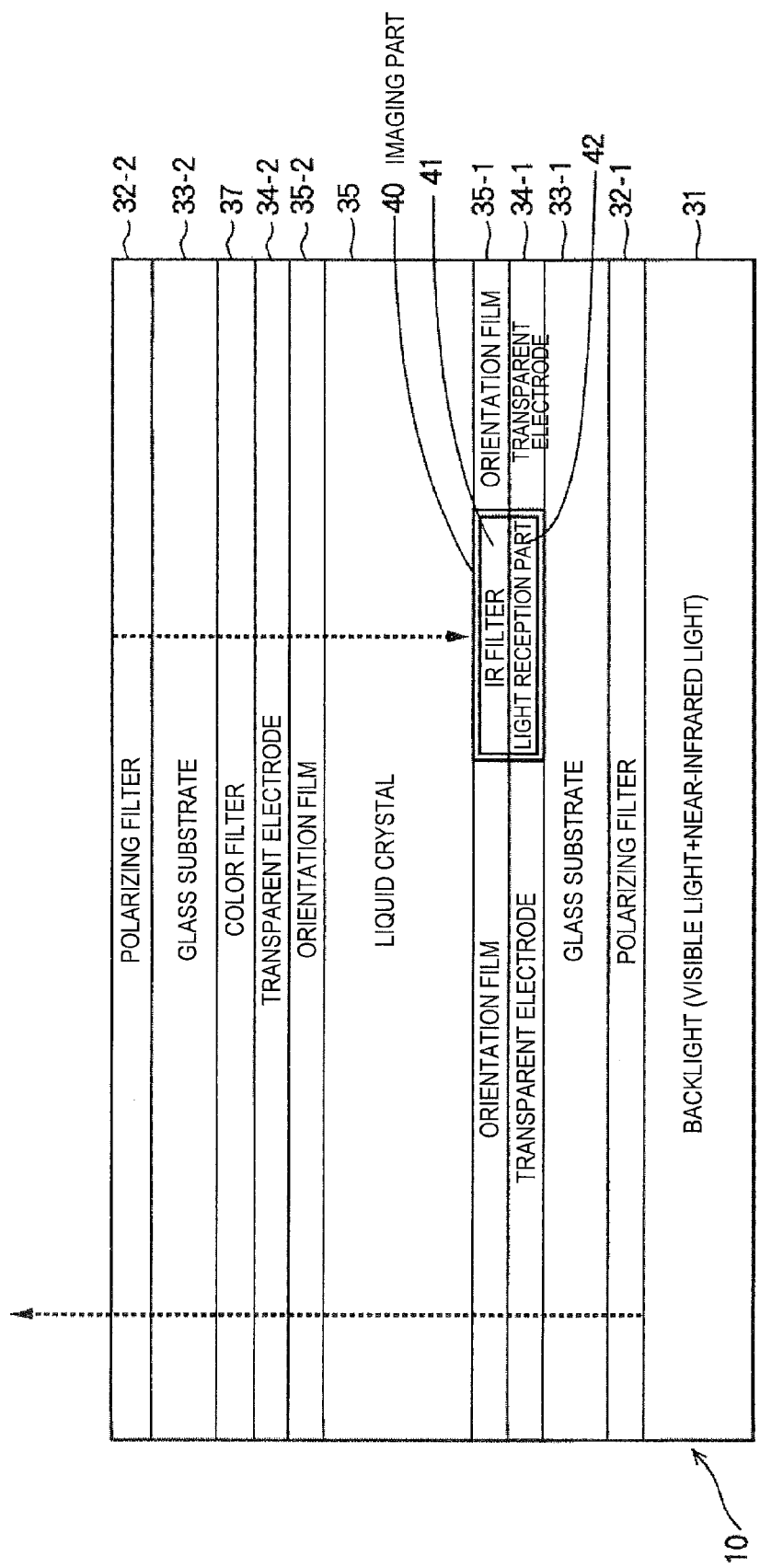
FIG. 6 is a cross-sectional view of the display.

FIG. 6 is a cross-sectional view of the display 10. This display 10 displays a screen corresponding to a display signal supplied from the measurement apparatus according to the embodiment. Moreover, the display 10 has an imaging part inside. The imaging part 40 images the surface of the display 10 from the inside and outputs the resulting imaging signal indicating a shape of the palms or the like of the subject touching the surface of the display 10 to the measurement apparatus.

The display 10 is configured by laminating a backlight 31, a polarizing filter 32-1, a glass substrate 33-1, a transparent electrode 34-1, an orientation film 35-1, liquid crystal 36, an orientation film 35-2, a transparent electrode 34-2, a color filter 37, a glass substrate 33-2, and a polarizing filter 32-2 in this order from the inside. Further, inside the glass substrates 33-1 and 33-2, the imaging part 40 imaging using near-infrared light is provided.

That is, the display 10 is configured to include the imaging part 40 inside a general configuration of a liquid crystal display. Meanwhile, the backlight 31 also emits near-infrared light (800 to 900 nm) for irradiating the bottom of the physical subject and the imaging part 40 receiving the light thus reflected along with the visible light for screen display.

The imaging part 40 is configured to include an IR filter 41 transmitting only the near-infrared light and a light reception part 42 receiving the near-infrared light to convert into an imaging signal. For the light reception part 42, for example, a technique utilizing photocurrent generated in an active layer or a technique utilizing accumulation of charge generated by light absorption can be used. In addition, when the light reception part 42 is saturated by too strong near-infrared light, the strength of the near-infrared light is adjusted by the orientation films 35-1 and 35-2, and thus, the intensity of the near-infrared light inputted to the light reception part 42 can be attenuated. Since the plural imaging parts 40 are arranged two-dimensionally and periodically for as many pixels displayed or for as many groups of predetermined number of pixels displayed, the imaging signals outputted from all the imaging parts 40 indicate the palm or the like of the subject touching the surface of the display 10.

In addition, the display 10 is not necessarily a liquid crystal display as illustrated in FIG. 6 but may be an organic EL display or a plasma display as long as it includes the imaging parts 40 inside.

(Constitutional Example of the Measurement Apparatus)

Figure 7:
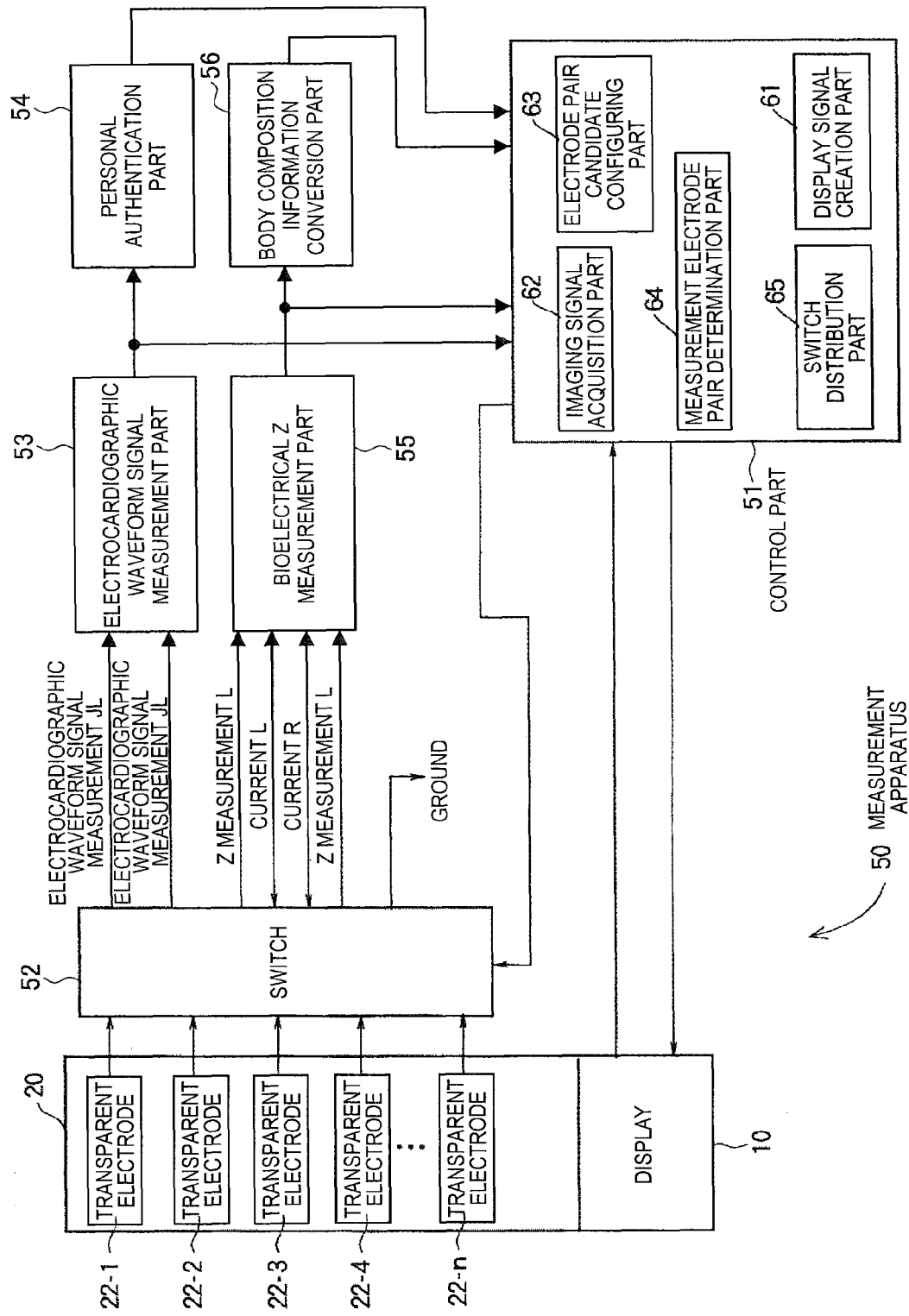
FIG. 7 is a block diagram illustrating a constitutional example of a measurement apparatus according to an embodiment of the present disclosure.

FIG. 7 illustrates a constitutional example of a measurement apparatus according to an embodiment of the present disclosure. This measurement apparatus 50 is configured to include a control part 51, a switch 52, an electrocardiographic waveform signal measurement part 53, a personal authentication part 54, a bioelectrical impedance (bioelectrical Z) measurement part 55, and a body composition information conversion part 56.

The control part 51 includes a display signal creation part 61, an imaging signal acquisition part 62, an electrode pair candidate configuring part 63, a measurement electrode pair determination part 64, and a switch distribution part 65.

The display signal creation part 61 creates a display signal corresponding to screen display of the display to output to the display 10. The imaging signal acquisition part 62 acquires the imaging signal from the imaging parts 40 included inside the display 10. The electrode pair candidate configuring part 63 specifies positions of the right and left palms of the subject based on the acquired imaging signal, and configures combinations of one or more transparent electrodes 22 which are estimated large in area which the subject touches with the left palm and one or more transparent electrodes 22 which are estimated large in area which it touches with the right palm (hereinafter, referred to as electrode pair candidates). The measurement electrode pair determination part 64 determines a measurement electrode pair from the configured electrode pair candidates.

The switch distribution part 65 distributes, out of the plural transparent electrodes 22-1 to 22-$n$ connected to the switch 52, those which are configured as the electrode pair candidates to the downstream (the electrocardiographic waveform signal measurement part 53, the bioelectrical impedance measurement part 55, or a ground), and releases the others. Moreover, the switch distribution part 65 distributes, out of the plural transparent electrodes 22-1 to 22-$n$ connected to the switch 52, those which are determined as the measurement electrode pair to the downstream, and releases the others.

In accordance with the control of the switch distribution part 65, the switch 52 connects those which are configured as the electrode pair candidates or those which are determined as the measurement electrode pair out of the connected plural transparent electrodes 22-1 to 22-$n$ to the downstream.

The electrocardiographic waveform signal measurement part 53 acquires an electrocardiographic waveform signal of the subject from the transparent electrodes 22 connected thereto via the switch 52 to output to the control part 51 and the personal authentication part 54. The personal authentication part 54 extracts a feature amount from the measured electrocardiographic waveform signal, and by comparing it with feature amounts of electrocardiographic waveform signals of previously registered persons, performs personal authentication of the subject. This authentication result is supplied to the display signal creation part 61 of the control part 51 and displayed on the display 10. The bioelectrical impedance measurement part 55 measures, using the transparent electrodes 22 connected thereto via the switch 52, a resistance value (bioelectrical impedance) of the subject to output to the control part 51 and the body composition information conversion part 56. Moreover, when measuring the bioelectrical impedance, it is desirable that at least two transparent electrodes are brought into contact with each of the right and left palms.

The body composition information conversion part 56 converts the measured bioelectrical impedance into body composition information (for example, a body fat percentage, muscle mass, bone mass or the like) using a previously held correspondence table, function or the like. This body composition information is supplied to the display signal creation part 61 of the control part 51 and displayed on the display 10.

(Operational Explanation)

Figure 8:
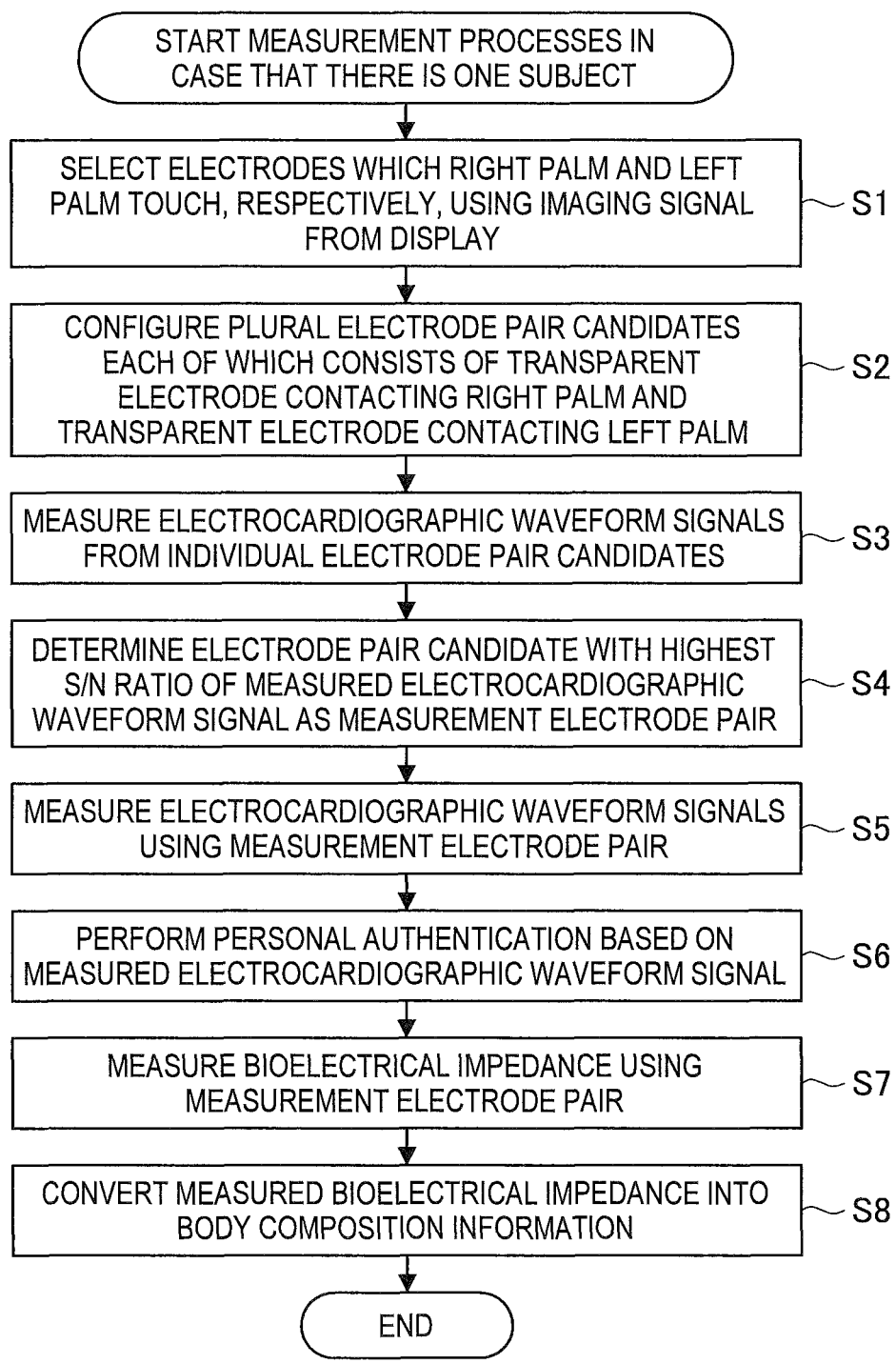
FIG. 8 is a flowchart for explaining measurement processes in the case that there is one subject.

FIG. 8 is a flowchart for explaining measurement processes in the case that there is only one subject, that is, under the circumstance of usage in which there is no chance that plural persons touch the surface of the display 10 simultaneously.

As a premise regarding the measurement processes, the one subject has already touched the surface of the display 10 with the both hands.

In step S1, the imaging signal acquisition part 62 of the control part 51 acquires an imaging signal from the imaging parts 40 of the display 10 to output to the electrode pair candidate configuring part 63. The electrode pair candidate configuring part 63 specifies positions of the right and left palms of the subject based on the imaging signal, and selects one or more transparent electrodes 22 which are estimated large in area which the subject touches with the left palm and one or more transparent electrodes 22 which are estimated large in area which it touches with the right palm.

In step S2, the electrode pair candidate configuring part 63 configures a plurality of electrode pair candidates consisting of combinations of one or more transparent electrodes 22 which are estimated as the subject touches them with the left palm and one or more transparent electrodes 22 which are estimated as touched with the right palm.

In step S3, the switch distribution part 65 distributes, out of the plurality of transparent electrodes 22-1 to 22-$n$ connected to the switch 52, those which are configured as the electrode pair candidates sequentially to the electrocardiographic waveform signal measurement part 53. The electrocardiographic waveform signal measurement part 53 measures electrocardiographic waveform signals corresponding to respective electrode pair candidates to output the measurement results to the control part 51.

In step S4, the measurement electrode pair determination part 64 of the control part 51 specifies, out of the electrocardiographic waveform signals measured from respective electrode pair candidates, the one with the highest S/N ratio, and determines the corresponding electrode pair candidate as a measurement electrode pair.

In step S5, the switch distribution part 65 distributes, out of the plurality of transparent electrodes 22-1 to 22-$n$ connected to the switch 52, the one which is configured as the measurement electrode pair to the electrocardiographic waveform signal measurement part 53. The electrocardiographic waveform signal measurement part 53 measures an electrocardiographic waveform signal obtained from the measurement electrode pair connected thereto via the switch 52 to output to the personal authentication part 54.

In step S6, the personal authentication part 54 extracts a feature amount from the measured electrocardiographic waveform signal, and by comparing it with feature amounts of electrocardiographic waveform signals of previously registered persons, performs personal authentication of the subject. This authentication result is supplied to the display signal creation part 61 of the control part 51 and displayed on the display 10.

In step S7, the bioelectrical impedance measurement part 55 measures, using the measurement electrode pair connected thereto via the switch 52, a bioelectrical impedance of the subject to output to the body composition information conversion part 56. In step S8, the body composition information conversion part 56 converts the measured bioelectrical impedance into body composition information. This body composition information is supplied to the display signal creation part of the control part 51 and displayed on the display 10. As above, the measurement processes in the case that there is only one subject are described.

According to the above described measurement processes, the subject can be allowed to touch the transparent electrodes to acquire an electrocardiographic waveform signal without causing the consciousness of their presence. And based on it, personal authentication of the subject can be performed. Moreover, out of the plurality of transparent electrodes 22, the best ones are selected and determined as a measurement electrode pair. Therefore, the electrocardiographic waveform signal and bioelectrical impedance can be measured in high accuracy.

Figure 9:
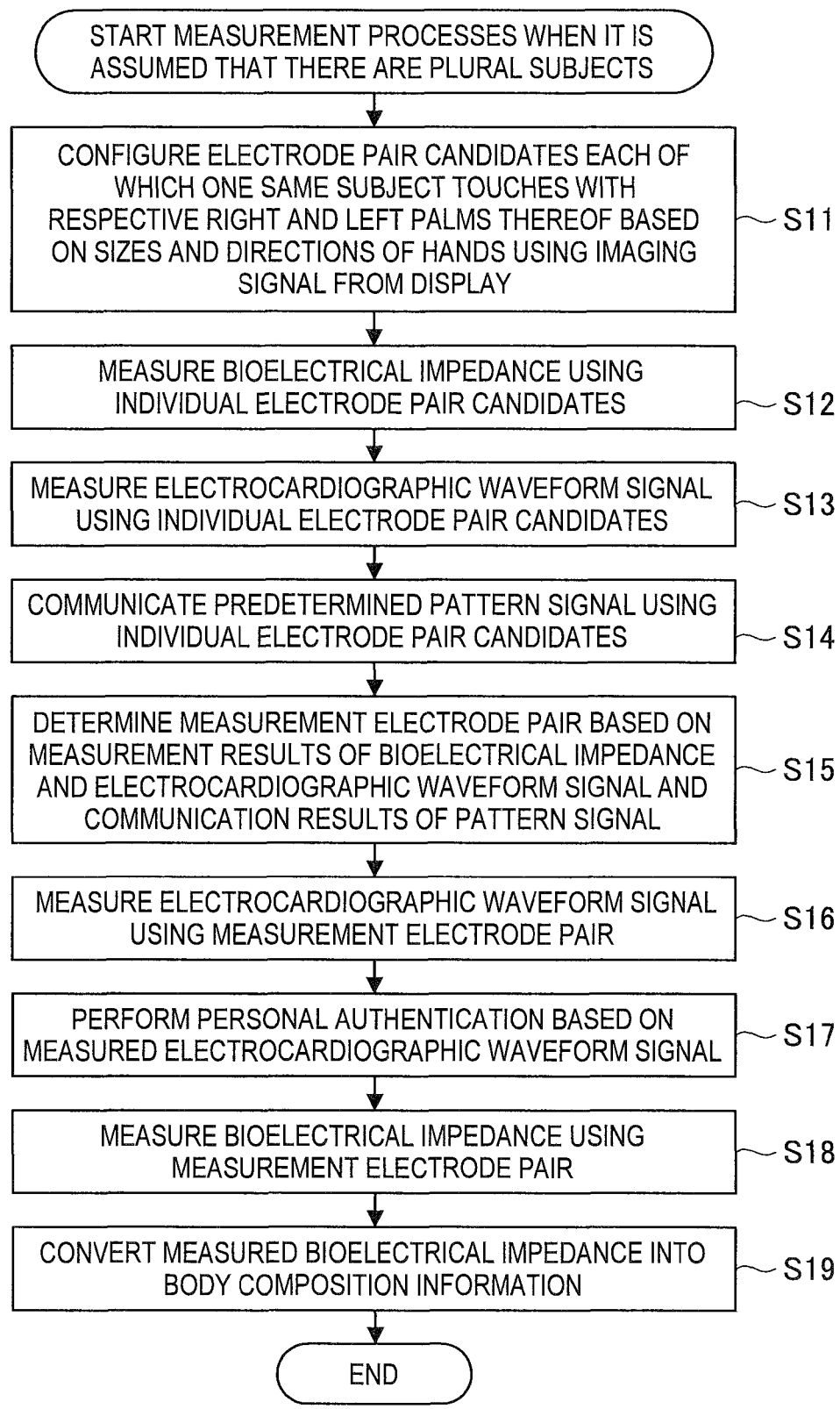
FIG. 9 is a flowchart for explaining measurement processes when it is assumed that plural persons touch the surface of the display simultaneously.

FIG. 9 is a flowchart for explaining measurement processes when it is assumed that plural persons touch the surface of the display 10 simultaneously.

As a premise regarding the measurement processes, plural persons including the subject are touching the surface of the display 10 with their both hands.

In step S11, the imaging signal acquisition part 62 of the control part 51 acquires an imaging signal from the imaging parts 40 of the display 10 to output to the electrode pair candidate configuring part 63. The electrode pair candidate configuring part 63 detects sizes and directions of palms touching the surface of the display 10 based on the imaging signal, and based on the detection results, selects one or more transparent electrodes 22 which are estimated to be touched with the left palm of one same person and one or more transparent electrodes 22 which are estimated to be touched with the right palm thereof. Further, the electrode pair candidate configuring part 63 configures a plurality of electrode pair candidates consisting of combinations of the one or more transparent electrodes 22 which are estimated to be touched with the left palm of the one same person and the one or more transparent electrodes 22 which are estimated to be touched with the right palm thereof.

In step S12, the switch distribution part 65 distributes, out of the plurality of transparent electrodes 22-1 to 22-$n$ connected to the switch 52, those which are configured as the electrode pair candidates sequentially to the bioelectrical impedance measurement part 55. The bioelectrical impedance measurement part 55 measures bioelectrical impedances corresponding to respective electrode pair candidates to output the measurement results to the control part 51. The measurement electrode pair determination part 64 of the control part 51 detects, out of the bioelectrical impedances measured from respective electrode pair candidates, those which are out of the range of values which measurement of human bodies can afford, and excludes the electrode pair candidates which detect those from the candidates for a measurement electrode pair.

In step S13, the switch distribution part 65 distributes, out of the plurality of transparent electrodes 22-1 to 22-$n$ connected to the switch 52, those which are configured as the electrode pair candidates sequentially to the electrocardiographic waveform signal measurement part 53. The electrocardiographic waveform signal measurement part 53 measures electrocardiographic waveform signals corresponding to respective electrode pair candidates to output the measurement results to the control part 51. The measurement electrode pair determination part 64 of the control part 51 detects, out of the electrocardiographic waveform signals measured from respective electrode pair candidates, those which are out of the range of waveforms which measurement of one same human body can afford, and excludes the electrode pair candidates which detect those from the candidates for the measurement electrode pair.

In step S14, the switch distribution part 65 distributes, out of the plurality of transparent electrodes 22-1 to 22-$n$ connected to the switch 52, those which are configured as the electrode pair candidates sequentially to the bioelectrical impedance measurement part 55. The bioelectrical impedance measurement part 55 sends a predetermined pattern signal (for example, 11001010) as an ASK modulation signal from one of respective electrode pair candidates, receives it through the other, and outputs the communication results to the control part 51. The measurement electrode pair determination part 64 of the control part 51 detects, out of the communication results of respective electrode pair candidates, those with which the correct pattern signal is not received, and excludes the electrode pair candidates which detect those from the candidates for the measurement electrode pair.

In step S15, the measurement electrode pair determination part 64 of the control part 51 determines the electrode pair candidate which remains through the processes in steps S12 to S14 without exclusion as the measurement electrode pair. In addition, when the plural electrode pair candidates remain, the one with the highest S/N ratio of the electrocardiographic waveform signal measured by the process in step S13 is determined as the measurement electrode pair.

At this stage, one of the plural persons touching the surface of the display 10 has been designated as the subject. Since the following processes in steps S16 to S19 are the same as the above-mentioned processes in steps S6 to S8 in FIG. 8, the description for those is omitted.

For the purpose that electrocardiographic waveform signals or the like are measured and personal authentication is performed for all the persons touching the surface of the display 10, it is adequate to repeat the processes in and after step S11 again without using the transparent electrodes 22 designated as the measurement electrode pair corresponding to the subject at this stage. As above, the measurement processes when it is assumed that the plural persons touch the surface of the display 10 simultaneously are described.

According to the above described measurement processes, the subject can be allowed to touch the transparent electrodes to acquire an electrocardiographic waveform signal without causing the consciousness of their presence. And based on it, personal authentication of the subject can be performed. Moreover, out of the plurality of transparent electrodes 22, the best ones are selected and determined as a measurement electrode pair. Therefore, the electrocardiographic waveform signal and bioelectrical impedance can be measured in high accuracy.

Incidentally, the series of the above-mentioned processes may be performed by hardware and performed by software. When the series of the processes are performed by software, a program constituting the software is installed from program recording media in a computer built in exclusive hardware, or one which can perform various kinds of functions by installing various kinds of programs, for example, such as a general-use personal computer.

Figure 10:
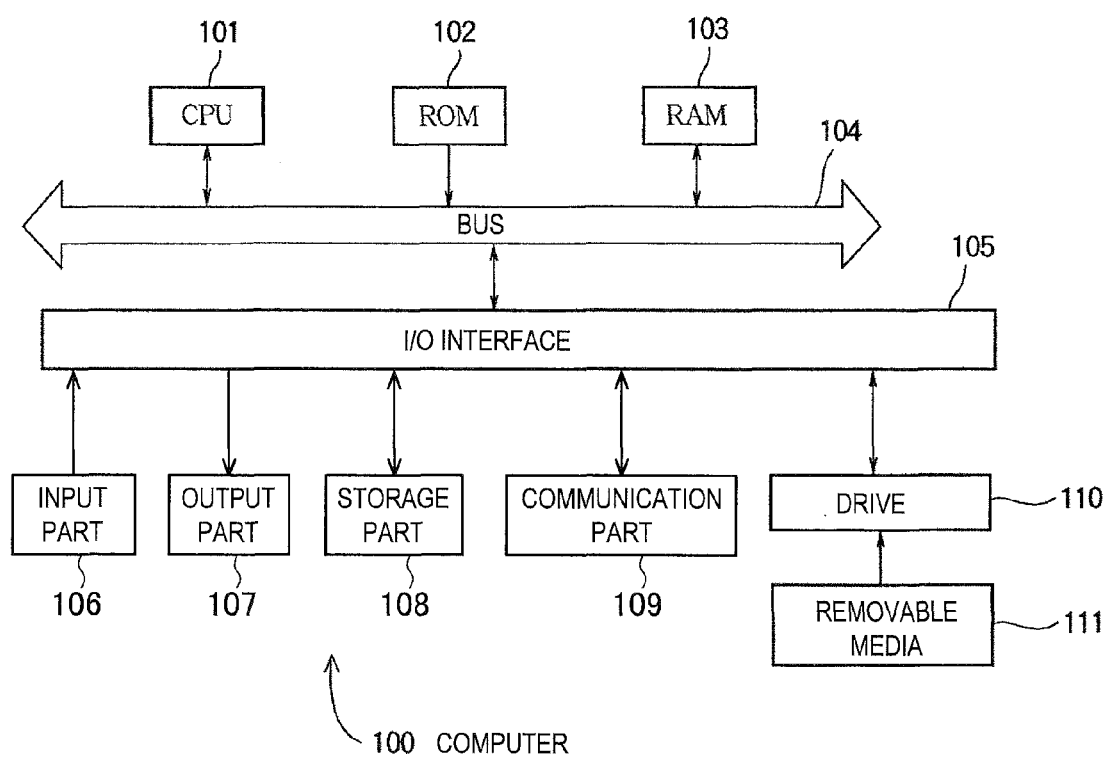
FIG. 10 is a block diagram illustrating a constitutional example of a computer.

FIG. 10 is a block diagram illustrating a constitutional example of hardware of a computer performing the series of the above-mentioned processes in accordance with a program.

In a computer 100, CPU (Central Processing Unit) 101, ROM (Read Only Memory) 102 and RAM (Random Access Memory) 103 are connected mutually by a bus 104.

An I/O interface 105 is further connected to the bus 104. To the I/O interface 105, an input part 106 including a keyboard, mouse, microphone and the like, an output part 107 including a display, loud speaker and the like, a storage part 108 including a hard disk drive, non-volatile memory and the like, a communication part 109 including network interface and the like, and a drive 110 driving removable media 111 such as a magnetic disk, optical disk, magneto-optical disk or semiconductor memory are connected.

In the computer 100 configured as above, the CPU 101 loads, for example, a program stored in the storage part 108 into the RAM 103 via the I/O interface 105 and bus 104 to execute it and thereby, the series of the above-mentioned processes are performed.

In addition, the program which the computer executes may serve as a program according to which the processes are performed chronologically in the order described in the present specification, or a program according to which the processes are performed in parallel or at a required timing of being called or the like.

Moreover, the program may serve as one which is processed by one computer or one which is processed by plural computers in distributed processing. Further, the program may serve as one which is executed by being transferred to a remote computer.

Embodiments according to the present disclosure are not limited to the above-mentioned embodiments but various modifications may occur within the spirit and scope of the present disclosure.

What is claimed is:

1. A measurement apparatus comprising:
    a plurality of transparent electrodes provided on a surface of a display;
    an acquisition part acquiring an imaging signal obtained by imaging the surface of the display from an inside of the display when a subject touches the surface of the display;
    a configuring part configuring electrode pair candidates from the plurality of transparent electrodes based on an acquired imaging signal from the acquisition part;
    an electrocardiographic waveform signal measurement part measuring electrocardiographic waveform signals of the subject using respective electrode pair candidates configured; and
    a determination part determining a measurement electrode pair from the electrode pair candidates based on the electrocardiographic waveform signals measured using the respective electrode pair candidates.

2. The measurement apparatus according to claim 1, wherein
    the electrocardiographic waveform signal measurement part further measures an electrocardiographic waveform signal using the determined measurement electrode pair.

3. The measurement apparatus according to claim 2, further comprising
    an authentication processing part performing authentication process of the subject based on the measured electrocardiographic waveform signal.

4. The measurement apparatus according to claim 2, wherein
    the determination part determines the measurement electrode pair from the electrode pair candidates based on S/N ratios of the electrocardiographic waveform signals measured using respective electrode pair candidates.

5. The measurement apparatus according to claim 2, wherein
    the determination part determines the measurement electrode pair from the electrode pair candidates based on communication results in communications of a predetermined pattern signal via respective electrode pair candidates.

6. The measurement apparatus according to claim 2, further comprising
    a bioelectrical impedance measurement part measuring a bioelectrical impedance of the subject using the determined measurement electrode pair.

7. The measurement apparatus according to claim 6, wherein
    the bioelectrical impedance measurement part further measures bioelectrical impedances of the subject using respective electrode pair candidates selected, and
    the determination part determines the measurement electrode pair from the electrode pair candidates based on the bioelectrical impedances measured using respective electrode pair candidates for plural subjects touching the surface of the display.

8. A measurement method for a measurement apparatus measuring an electrocardiographic waveform signal of a subject, comprising, by the measurement apparatus:

acquiring an imaging signal obtained by imaging a surface of a display from an inside of the display when the subject touches the surface of the display, a plurality of transparent electrodes being provided on the surface;

configuring electrode pair candidates from the plurality of transparent electrodes based on the acquired imaging signal;

measuring electrocardiographic waveform signals of the subject using respective electrode pair candidates configured; and determining a measurement electrode pair from the electrode pair candidates based on the electrocardiographic waveform signals measured using respective electrode pair candidates.

9. A program stored on a non-transitory medium causing a computer to function as:

an acquisition part acquiring an imaging signal obtained by imaging a surface of a display from an inside of the display when a subject touches the surface of the display, a plurality of transparent electrodes being provided on the surface;

a configuring part configuring electrode pair candidates from the plurality of transparent electrodes based on an acquired imaging signal from the acquisition part;

an electrocardiographic waveform signal measurement part measuring electrocardiographic waveform signals of the subject using respective electrode pair candidates configured; and a determination part determining a measurement electrode pair from the electrode pair candidates based on the electrocardiographic waveform signals measured using respective electrode pair candidates.

10. An information processing apparatus comprising:

a plurality of transparent electrodes provided on a surface of a display;

an acquisition part acquiring an imaging signal obtained by imaging the surface of the display from an inside of the display when a subject touches the surface of the display;

a configuring part configuring electrode pair candidates from the plurality of transparent electrodes based on an acquired imaging signal from the acquisition part;

an electrocardiographic waveform signal measurement part measuring electrocardiographic waveform signals of the subject using respective electrode pair candidates configured or a measurement electrode pair to be determined;

a determination part determining the measurement electrode pair from the electrode pair candidates based on the electrocardiographic waveform signals measured using respective electrode pair candidates; and a signal processing part performing a predetermined process based on the electrocardiographic waveform signal measured using the measurement electrode pair.

* * * * *